United States Patent [19]
Rodarte

[11] Patent Number: 6,135,115
[45] Date of Patent: Oct. 24, 2000

[54] MULTI-DIRECTIONAL AND ADJUSTABLE BELT FOR FIXATION OF THE HUMAN BODY ON REMOVAL BOARDS AND SIMILAR

[76] Inventor: Luiz Henrique Cosso Rodarte, R. Estilac, 185-São Paulo-SP, Brazil

[21] Appl. No.: 09/348,707

[22] Filed: Jul. 7, 1999

[30] Foreign Application Priority Data

Jul. 8, 1998 [BR] Brazil .................................. 7801276 U

[51] Int. Cl.[7] .................................................. A61B 19/00
[52] U.S. Cl. ........................... 128/869; 128/870; 128/876
[58] Field of Search ..................................... 128/846, 869, 128/870, 875, 876; 5/624, 625, 626, 630

[56] References Cited

U.S. PATENT DOCUMENTS 3,933,154   1/1976   Cabansag .................................. 128/870
4,841,961   6/1989   Burlage .................................... 128/876
5,014,374   5/1991   Williams .................................. 128/870

Primary Examiner—Michael A. Brown
Attorney, Agent, or Firm—Wood, Herron & Evans, LLP

[57] ABSTRACT

MULTI-DIRECTIONAL AND ADJUSTABLE BELT FOR FIXATION OF THE HUMAN BODY ON REMOVAL BOARDS AND SIMILAR are characterized by a longitudinal belt (1) whose inferior extreme presents a connection belt (2) whereas the superior extreme incorporates a transversal fixed belt (3) whereas the longitudinal belts (4) which on their back extremes (9) incorporate female receptacles (8) and on the frontal extreme (15) male hooks (10) whereas the longitudinal belt (1) receives three transversal sliding belts (6) which in their back extremes (8) and on the frontal extremes (15) male hooks (10) which in their median section are provided with a sliding ring (7) which in their interior incorporates a rigid PVC plate (20) and said sliding ring (7) crosses whit the longitudinal belt (1).

1 Claim, 4 Drawing Sheets

MULTI-DIRECTIONAL AND ADJUSTABLE BELT FOR FIXATION OF THE HUMAN BODY ON REMOVAL BOARDS AND SIMILAR

The present patent refers to a model of utility of one MULTI-DIRECTIONAL AND ADJUSTABLE BELT FOR FIXATION OF THE HUMAN BODY ON REMOVAL BOARDS AND SIMILAR, which has been developed in order to improve safety and ease the transportation of injured or sick patients to hospitals and medical centers.

When one person suffers an accident, such as: a fall from altitudes, run-overs, car, bicycle, motorcycle accidents and other kinds of accidents, it is recommended that the patient be transported immobilized the best way possible. This measure views to avoid the seriousness of the patient, when a broken rib may perforate the lungs and other organs, among others complications, such as: dislodgement of the cervical column, aggravation of fractures.

It is noted that the existing belts for fastening the human body are made of one single longitudinal piece from which 5 double belts are incorporated transversally or by independent belts which through or male and female hooks making the work slow and not guaranteeing safety to the patient as in case patient moves in excess or abruptly the belts turn loose, putting at risk patient's health state or even his life.

Therefore, we can state and assure that with the existing belts for tying up human body; they are fixed on the removal boards without any guarantee of an adequate and ideal positioning of the body in its longitudinal direction, a primordial condition to protect the cervical column and the neck, especially because of the fact that the belts are tied only on the transversal direction, thus the strength of the tying are not distributed homogeneously.

On account of this and other inconveniences not mentioned, the inventor, after a long period of studies developed the MULTI-DIRECTIONAL AND ADJUSTABLE BELT FOR FIXATION OF THE HUMAN BODY ON REMOVAL BOARDS AND SIMILAR which is fundamented as from an adjustable longitudinal belt which is elevated by a connecting belt destined to fix the patient's feet, as well as to support them when there is need to put the board on the upright position, whereas on the top the longitudinal belt is elevated by one transversal and fixed belt whose ends extend by the static, adjustable, transversal lines, destined to tied up the superior limbs on the line of the armpit of the human body. At the extremes of the fixed belt transversally paralel adjustable longitudinal belts arise which pass over the clavicle and fix the trunk of the extremes of the board, leaving the head and the neck between said paralel belts.

The longitudinal belt receives three sliding transversal belts which incorporate a sliding ring which receives a hard PVC plate in order to stabilize the ring which crosses with the longitudinal belt, and on the back extremes of the transversal belts, pointers receptacle female and the frontal extremes are fitted with sliding belts destined to tied up the patient above the navel, at the height of the elbows, on the pelvis, at the height of the crests and on the knees, impeding its flexion.

The static transversal belt, the sliding belts and the longitudinal belts form connections that are by eyes included on the removal board thus guaranteeing the fixation of the body on the board and above all guaranteeing an adjustable of the body on the board. It is valid to mention that with this tying, patient although moving in excess or abruptly cannot get free from the belts.

In order to investigate more clearly what has been developed, please find enclosed illustrative drawing which references numerically in conjunction with a description in detail where the:

Figure 1:
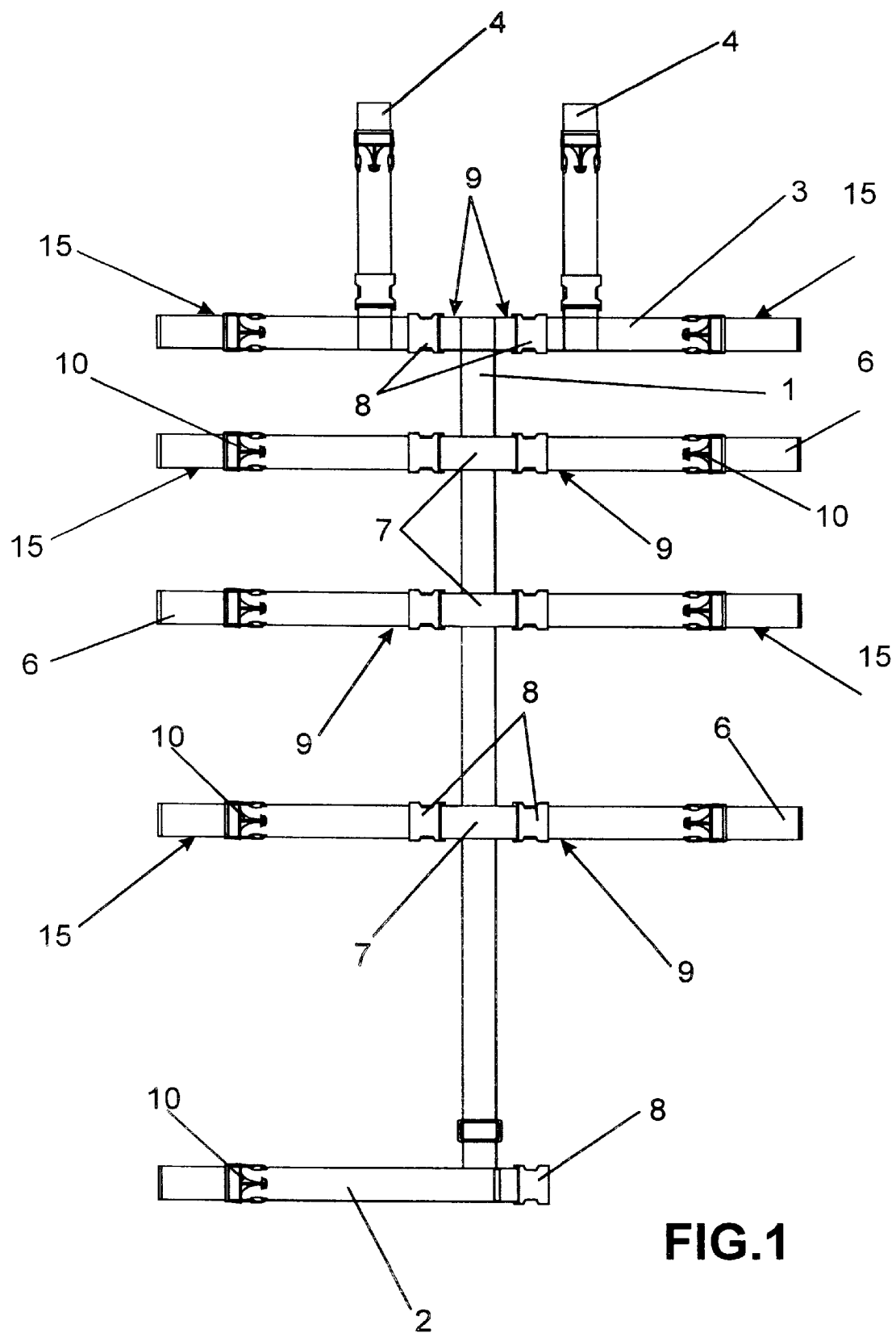
FIG. 1 shows the open belt.
Figure 2:
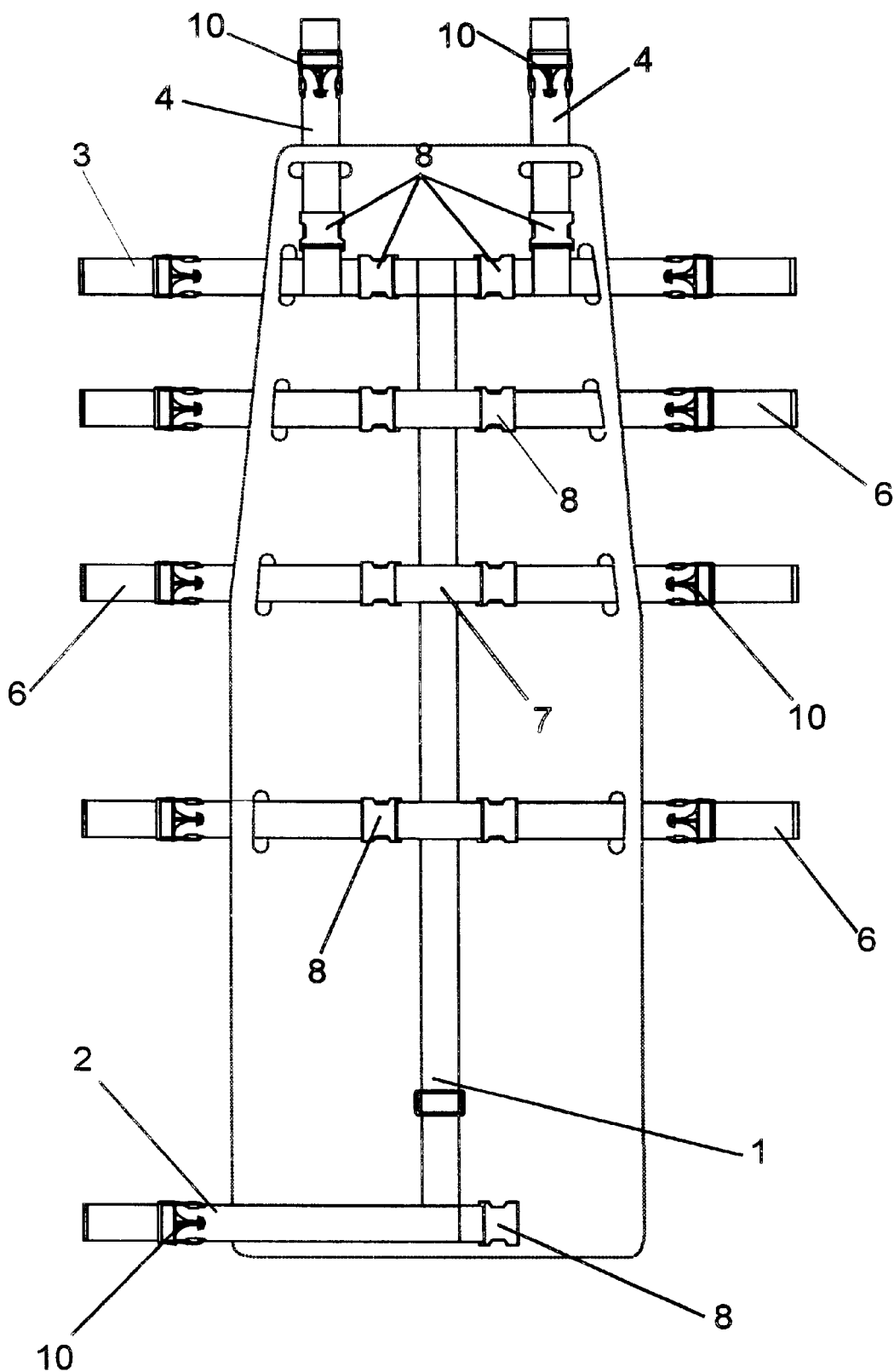
FIG. 2 shows the belt introduced in the board.
Figure 3:
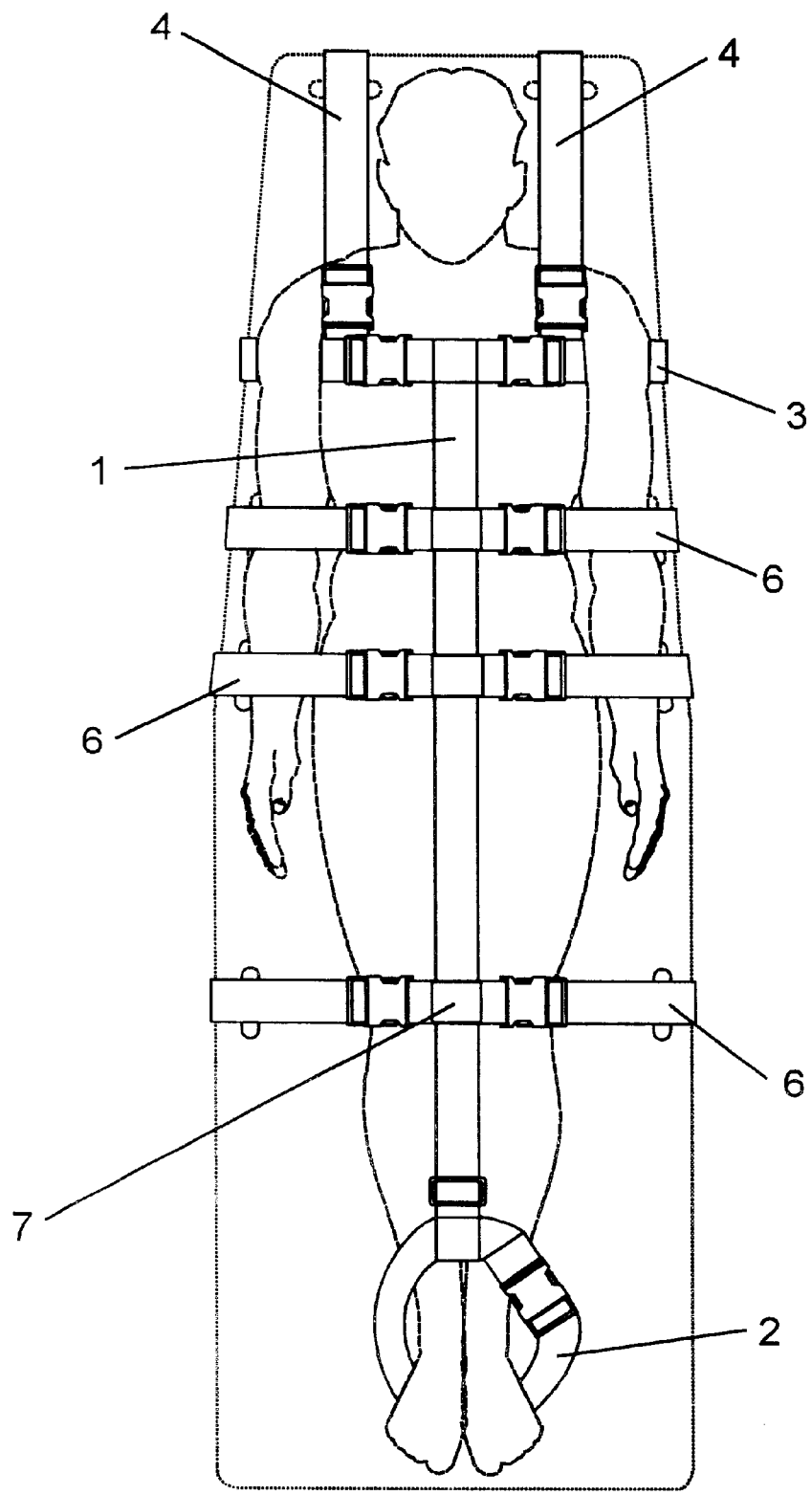
FIG. 3 shows the up of the belt on a patient.
Figure 4:
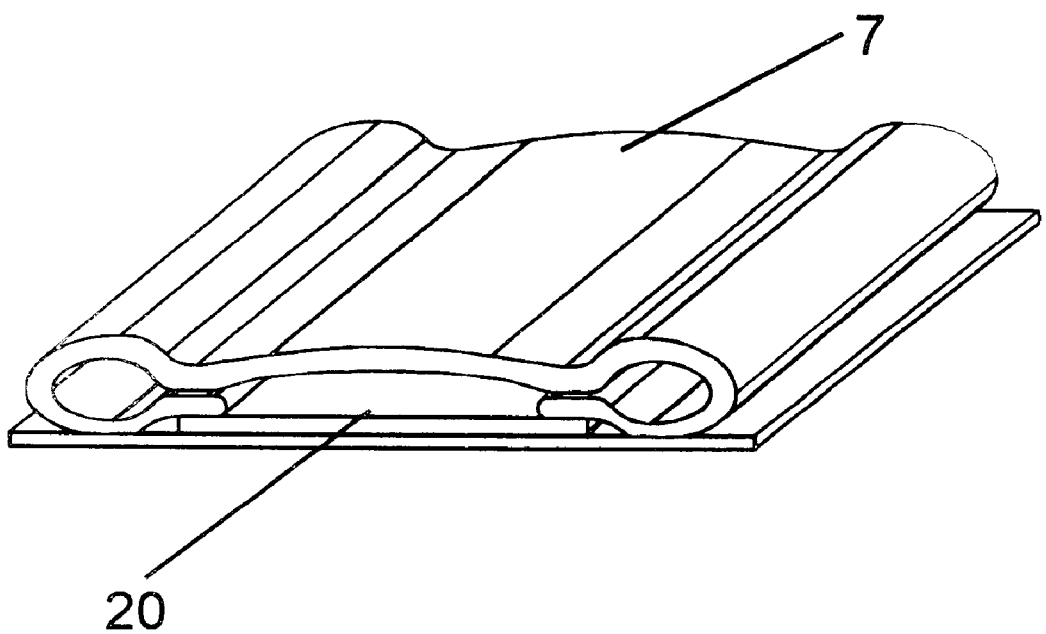
FIG. 4 shows a detail in perspective referring to rigid PVC in the interior of the sliding ring.

As the drawings show, we can note that the MULTI-DIRECTIONAL AND ADJUSTABLE BELT FOR FIXATION OF HUMAN BODY ON REMOVAL BOARDS AND SIMILAR are formed by a longitudinal belt (1) which the inferior extremes presents the connection belt (2) whereas the superior extreme incorporates a transversal fixed belt (3) where from projects in spaces parallel longitudinal belts (4) which in their back extremes (9) that is, the portion of the longitudinal belts (4) proximate to the fixed belt (3), as seen in FIG. 1, incorporate female receptacles (8) and on the frontal extreme (15), that is, the portion of the longitudinal belts (4) distal from the fixed belt (3), as seen in FIG. 1, male hooks (10), whereas the longitudinal belt (1) receives three sliding transversal belts (6) which in their back extremes (9), that is, the portions of the sliding belts (6) proximate to the longitudinal belt (1), as seen in FIG. 1, incorporates female receptacles (8) and on the frontal extremes (15), that is, the portions of the sliding belts (6) distal from the longitudinal belt (1), as seen in FIG. 1, male hooks (10) which in median section are fitted with sliding ring (7) which in its interior incorporates a rigid PVC plate (20). The said sliding ring (7) crosses with the longitudinal belt (1).

What is claimed is:

1. A multi-directional and adjustable belt for fixation of the human body on removal boards and similar, comprising:

a longitudinal belt (1) having an inferior extreme and a superior extreme;

a connection belt (2) attached to said longitudinal belt (1) at said inferior extreme;

a transversal fixed belt (3) attached to said longitudinal belt (1) at said superior extreme;

a pair of longitudinal belts (4) having back extremes (9) with female receptacles (8) and frontal extremes (15) having male hooks (10); and three transversal sliding belts (6) having back extremes (9) with female receptacles (8) and frontal extremes (15) having male hooks (10), said transversal sliding belts (6) having respective median sections provided with a sliding ring (7) having an interior rigid PVC plate (20), said sliding ring (7) adapted to receive said longitudinal belt (1) therethrough.

* * * * *